United States Patent
Pois et al.

(10) Patent No.: US 10,082,390 B2
(45) Date of Patent: Sep. 25, 2018

(54) FEED-FORWARD OF MULTI-LAYER AND MULTI-PROCESS INFORMATION USING XPS AND XRF TECHNOLOGIES

(71) Applicant: ReVera, Incorporated, Santa Clara, CA (US)

(72) Inventors: Heath A. Pois, Fremont, CA (US); Wei Ti Lee, San Jose, CA (US); Lawrence V. Bot, Maple Grove, MN (US); Michael C. Kwan, Sunnyvale, CA (US); Mark Klare, Poughkeepsie, NY (US); Charles Thomas Larson, Belmont, CA (US)

(73) Assignee: NOVA MEASURING INSTRUMENTS INC., Santa Clara, CA (US)

( * ) Notice: Subject to any disclaimer, the term of this patent is extended or adjusted under 35 U.S.C. 154(b) by 89 days.

(21) Appl. No.: 15/322,093

(22) PCT Filed: Jun. 19, 2015

(86) PCT No.: PCT/US2015/036619
§ 371 (c)(1),
(2) Date: Dec. 23, 2016

(87) PCT Pub. No.: WO2015/200112
PCT Pub. Date: Dec. 30, 2015

(65) Prior Publication Data
US 2017/0160081 A1 Jun. 8, 2017

Related U.S. Application Data

(60) Provisional application No. 62/016,211, filed on Jun. 24, 2014.

(51) Int. Cl.
*G01B 15/02* (2006.01)
*G01N 23/223* (2006.01)
*G01N 23/2273* (2018.01)

(52) U.S. Cl.
CPC .......... *G01B 15/02* (2013.01); *G01N 23/223* (2013.01); *G01N 23/2273* (2013.01)

(58) Field of Classification Search
CPC ...... G01B 15/02; G01N 23/22; G01N 23/223; G01N 23/2273
See application file for complete search history.

(56) References Cited

U.S. PATENT DOCUMENTS

| 9,240,254 B2 | 1/2016 | Schueler et al. | |
| 2013/0077742 A1* | 3/2013 | Schueler | G21K 1/06 378/44 |

(Continued)

OTHER PUBLICATIONS

International Preliminary Report on Patentability for PCT Patent Application No. PCT/US2015/036619 dated Jan. 5, 2017, 16 pgs.

(Continued)

*Primary Examiner* — Casey Bryant
(74) *Attorney, Agent, or Firm* — Womble Bond Dickinson (US) LLP; Joseph Bach, Esq.

(57) ABSTRACT

Methods and systems for feed-forward of multi-layer and multi-process information using XPS and XRF technolgies are disclosed. In an example, a method of thin film characterization includes measuring first XPS and XRF intensity signals for a sample having a first layer above a substrate. A thickness of the first layer is determined based on the first XPS and XRF intensity signals. The information for the first layer and for the substrate is combined to estimate an effective substrate. Second XPS and XRF intensity signals are measured for a sample having a second layer above the first layer above the substrate. The method also involves determining a thickness of the second layer based on the (Continued)

second XPS and XRF intensity signals, the thickness accounting for the effective substrate.

20 Claims, 9 Drawing Sheets

(56) References Cited

U.S. PATENT DOCUMENTS

2015/0308969 A1 10/2015 Pois et al.
2017/0160081 A1* 6/2017 Pois .................. G01B 15/02

OTHER PUBLICATIONS

Lothongkum, G., et al., "XPS investigation of surface film on high Cr—Ni ferritic and austenitic stainless steels", Elsevier, Applied Surface Science 218, 2003, pp. 202-209.
Martin, A., et al., "Preparation of transparent and conductive Al-doped ZnO thin films by ECR plasma enhanced CVD", Elsevier, Surface and Coatings Technology 151-152, 2002, pp. 289-293.
Wakiya, Naoki, et al., "An XPS study of the nicleation and growth behavior of an epitaxial Pb(Zr,Ti)O3/MgO(100) thin film prepared by MOCVD", Elsevier, Thin Solid Films 372, 2000, pp. 156-162.
international Search Report and Written Opinion from PCT/U82015/036619 dated Oct. 22, 2015, 20 pgs.
van den Berg, J. A. et al., "High resolution depth profile analysis of ultra thin high-k HF based films using MEIS compared with XTEM, XRF, SE and MCPS," ECS Transactions, 25 (3) 349-361 (2009).

* cited by examiner

FEED-FORWARD OF MULTI-LAYER AND MULTI-PROCESS INFORMATION USING XPS AND XRF TECHNOLOGIES

CROSS-REFERENCE TO RELATED APPLICATIONS

This application is a U.S. National Phase application under 35 U.S.C. § 371 of International Application No. PCT/US2015/036619, filed Jun. 19, 2015, entitled "FEED-FORWARD OF MULTI-LAYER AND MULTI-PROCESS INFORMATION USING XPS AND XRF TECHNOLOGIES," which claims the benefit of U.S. Provisional Application No. 62/016,211, filed on Jun. 24, 2014, the entire contents of which are hereby incorporated by reference herein.

BACKGROUND

1) Field

Embodiments of the invention are in the field of semiconductor metrology and, in particular, methods and systems for feed-forward of multi-layer and multi-process information using X-ray photoelectron spectroscopy (XPS) analysis and X-ray fluorescence (XRF) analysis technologies.

2) Description of Related Art

X-ray photoelectron spectroscopy (XPS) is a quantitative spectroscopic technique that measures the elemental composition, empirical formula, chemical state and electronic state of the elements that exist within a material. XPS spectra may be obtained by irradiating a material with a beam of X-rays while simultaneously measuring the kinetic energy and number of electrons that escape from the top, e.g., 1 to 10 nm of the material being analyzed. XPS analysis commonly employs monochromatic aluminum Kα (AlKα) X-rays, which may be generated by bombarding an aluminum anode surface with a focused electron beam. A fraction of the generated AlKα X-rays is then intercepted by a focusing monochromator and a narrow X-ray energy band is focused onto the analysis site on a sample surface. The X-ray flux of the AlKα X-rays at the sample surface depends on the electron beam current, the thickness and integrity of the aluminum anode surface, and crystal quality, size, and stability of the monochromator.

X-ray fluorescence (XRF) is the emission of characteristic "secondary" (or fluorescent) X-rays from a material that has been excited by bombarding with higher energy X-rays or gamma rays. The phenomenon is widely used for elemental analysis and chemical analysis, particularly in the investigation of metals, glass, ceramics and building materials, and for research in geochemistry, forensic science and archaeology.

XPS analysis and XRF analysis each have their own advantages. However, advances are needed in analyses based on XPS and/or XRF detection.

SUMMARY

One or more embodiments are directed to methods and systems for feed-forward of multi-layer and multi-process information using XPS and XRF technologies.

In an embodiment, a method of thin film characterization includes measuring first XPS and XRF intensity signals for a sample having a first layer above a substrate. The first XPS and XRF intensity signals include information for the first layer and for the substrate. The method also involves determining a thickness of the first layer based on the first XPS and XRF intensity signals. The method also involves combining the information for the first layer and for the substrate to estimate an effective substrate. The method also involves measuring second XPS and XRF intensity signals for a sample having a second layer above the first layer above the substrate. The second XPS and XRF intensity signals include information for the second layer, for the first layer and for the substrate. The method also involves determining a thickness of the second layer based on the second XPS and XRF intensity signals, the thickness accounting for the effective substrate.

In another embodiment, a system for characterizing a thin film includes an X-ray source for generating an X-ray beam. The system also includes a sample holder for positioning a sample in a pathway of said X-ray beam. The system also includes a first detector for collecting an X-ray photoelectron spectroscopy (XPS) signal generated by bombarding said sample with said X-ray beam. The system also includes a second detector for collecting an X-ray fluorescence (XRF) signal generated by bombarding said sample with said X-ray beam. The system also includes a computing device configured to determine a thickness of a second layer of the sample based on the XPS and XRF signals. The determining the thickness accounts for an estimated effective substrate based on a first layer and a substrate of the sample, the first layer and substrate below the second layer of the sample.

In another embodiment, a non-transitory machine-accessible storage medium having instructions stored thereon which cause a data processing system to perform a method of method of thin film characterization. The method includes measuring first XPS and XRF intensity signals for a sample having a first layer above a substrate. The first XPS and XRF intensity signals include information for the first layer and for the substrate. The method also involves determining a thickness of the first layer based on the first XPS and XRF intensity signals. The method also involves combining the information for the first layer and for the substrate to estimate an effective substrate. The method also involves measuring second XPS and XRF intensity signals for a sample having a second layer above the first layer above the substrate. The second XPS and XRF intensity signals include information for the second layer, for the first layer and for the substrate. The method also involves determining a thickness of the second layer based on the second XPS and XRF intensity signals, the thickness accounting for the effective substrate.

In an embodiment, a method of thin film characterization includes measuring a first XPS intensity signal for a sample having a first layer above a substrate. The first XPS intensity signal includes information for the first layer and for the substrate. The method also involves determining a thickness of the first layer based on the first XPS intensity signal. The method also involves combining the information for the first layer and for the substrate to estimate an effective substrate. The method also involves measuring a second XPS intensity signal for a sample having a second layer above the first layer above the substrate. The second XPS intensity signal includes information for the second layer, for the first layer and for the substrate. The method also involves determining a thickness of the second layer based on the second XPS intensity signal, the thickness accounting for the effective substrate.

In an embodiment, a method of thin film characterization includes measuring a first XRF intensity signal for a sample having a first layer above a substrate. The first XRF intensity signal includes information for the first layer and for the substrate. The method also involves determining a thickness of the first layer based on the first XRF intensity signal. The method also involves combining the information for the first layer and for the substrate to estimate an effective substrate. The method also involves measuring a second XRF intensity signal for a sample having a second layer above the first layer above the substrate. The second XRF intensity signal includes information for the second layer, for the first layer and for the substrate. The method also involves determining a thickness of the second layer based on the second XRF intensity signal, the thickness accounting for the effective substrate.

DETAILED DESCRIPTION

Figure 1:
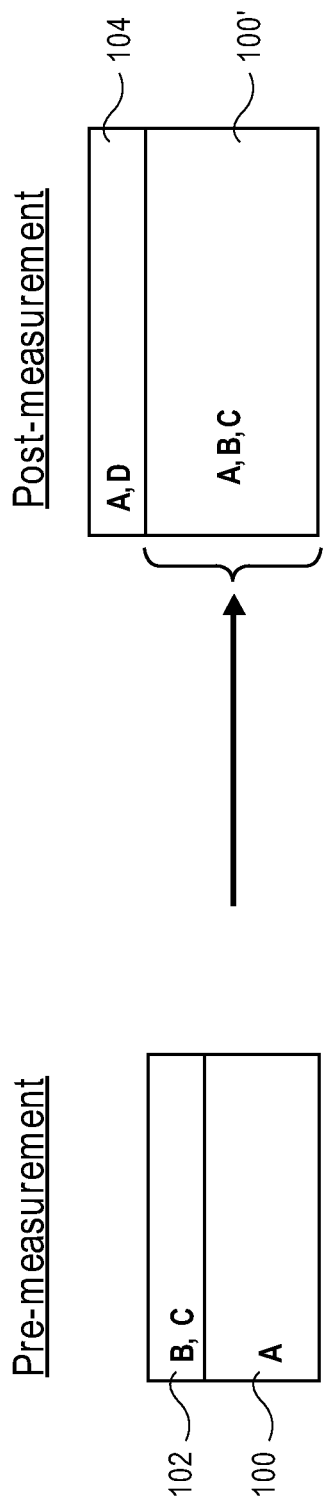
FIG. 1 is a basic schematic example that illustrates the XPS+XRF combined technology measurement choreography of XPS and/or XRF feed-forward, in accordance with an embodiment of the present invention.

Methods and systems for feed-forward of multi-layer and multi-process information using XPS and XRF technologies are described. In the following description, numerous specific details are set forth, such as approximation techniques and system arrangements, in order to provide a thorough understanding of embodiments of the present invention. It will be apparent to one skilled in the art that embodiments of the present invention may be practiced without these specific details. In other instances, well-known features such as entire semiconductor device stacks are not described in detail in order to not unnecessarily obscure embodiments of the present invention. Furthermore, it is to be understood that the various embodiments shown in the Figures are illustrative representations and are not necessarily drawn to scale.

To provide context, various electronic events may occur when a sample including a layer disposed above a substrate is bombarded with X-rays. For example, an electron may be released from the sample. X-ray photoemission may occur for an electron generated within the top, e.g., 10 nanometers of the sample. Most information from an XPS measurement is usually obtained near the surface since attenuation of the electron signal occurs as the electrons travel through material on their way out. For measurements deeper in the sample (e.g., 0.1-2 microns deep), X-ray fluorescence (XRF) may be used since XRF signals typically attenuate 1000 times less than XPS photoelectron signals and are thus less susceptible to effects of depth within a sample.

One or more embodiments described herein are directed to (1) the detection and use of photo-electron (XPS) and X-ray fluorescent (XRF) signals from single and multi-layer films to determine thickness and composition, along with (2) specification and algorithmic determination of feed-forward film information from a "pre" measurement operation to "post" process measurements in order to determine the most accurate and stable process control of thickness and composition. In some embodiments, the results from intermediate XPS/XRF process measurements are saved in a database that is simultaneously accessible to all measurement tools, enabling a feed-forward solution across a fleet of systems. More generally, embodiments are directed to measuring XPS and XRF signals, combining signals in a global, simultaneous fit using a film stack that properly accounts for the predicted XPS and XRF intensities at subsequent operations by direct or model-based methods.

To provide further context, one or more embodiments described herein may be implemented to address issues otherwise associated with simultaneous determination and process control of complex, multi-layer films having thickness and compositional material (atomic composition or AC %) that require stringent process control. By contrast, state-of-the-art approaches involve resolving such issues by spectroscopic ellipsometry and reflectometry or other traditional methods in an attempt to simultaneously determine the thickness and composition using a multi-operation feed forward methodology.

In accordance with an embodiment of the present invention, technical advantages of approaches described herein involve the use of XPS and XRF measurements while allowing for the use of fundamental measurement information from a pre measurement to be usefully employed in subsequent film models for post measurements. In one embodiment, such an approach provides a highly decoupled problem at each operation, which is unlike other technologies where the complexity of the previous films and results must be carried forward at each subsequent operation.

Implementation of certain embodiments described herein involves the combination of XPS and XRF signals along with realistic film stack models to simultaneously determine the thickness and compositional film properties in a multi-operation thickness and composition near the sample surface, the ability to feed-forward results from previous process/metrology operations into an increasingly thicker, more complex film stack fundamentally extends the capability of XPS (and in combination with XRF) for fab process control.

In more specific embodiments, since XPS and XRF are both intensity-based technologies, it is possible to effectively de-couple multi-operation measurements in a very clean and fundamental way by feeding forward pre results to the subsequent film substrate model information that specifies the relative intensity of the underlying species for post measurements. The effective substrate model at each operation contains the relevant species from the previous operation, and an intensity production factor that scales with the bulk AC % value from the previous measurement.

It is to be appreciated that XPS+XRF feed-forward approaches described herein may be implemented in several different ways. In an embodiment, the information fed forward can be model-independent, only depending on the fundamental atomic sensitivity factors (ASF's). In this case, intensity-only determined "bulk AC %" values at each operation are forwarded into an effective substrate model at the subsequent operation for the most accurate thickness and composition determination. In another embodiment, feeding forward thickness-only information may be sufficient, or a calculated effective substrate result may be used, and should be considered a complimentary approach contained within a broader scope of embodiments described herein. In any of the approaches described herein, in an embodiment, in order to enable the full feed-forward solution across single- and multiple systems in a fab environment, a database is required for real-time storing and retrieval of pre results.

As a representative example, FIG. 1 is a basic schematic example that illustrates the XPS+XRF combined technology measurement choreography of XPS and/or XRF feed-forward, in accordance with an embodiment of the present invention. Referring to FIG. 1, a first layer 102 is formed above a substrate 100. The first layer 102 includes species B and C, while the substrate 100 includes species A. For the pre-measurement operation, intensities from species A, B and C are measured, and composition and/or thickness is determined and stored in a database. A second layer 104 is then formed above the first layer 102. In one embodiment, the second layer 104 includes species A along with a new species D.

In an embodiment, for the post-measurement where the second layer 104 is deposited, the accurate determination of composition and/or thickness of the second layer 104 requires specification of only the effective intensity contribution of the original A,B,C signals from the pre-measurement. Thus, the first layer 102 and the substrate 100 are effectively treated as a single incoming layer or substrate 100' ("effective substrate). This can be enabled by direct AC % from intensities only, and/or model-derived results.

Referring again to FIG. 1, then, pre-measurement involves determination of first layer 102 thickness and composition. The relative intensities of species A, B and C are calculated. A feed forward of the information of the so-called previous layer with results for all relative intensities is then used in a post-measurement. The post-measurement involves a determination of the thickness and composition (e.g., species A and new species D) of the second layer 104. The determination accounts for the effective substrate 100'.

A first specific example of a multi-operation/multi-process film result using feed forward of XPS results is described below in association with FIGS. 2, 3 and 4. The example involves a titanium nitride (TiN)/high-k dielectric (HiK) sample.

Figure 2:
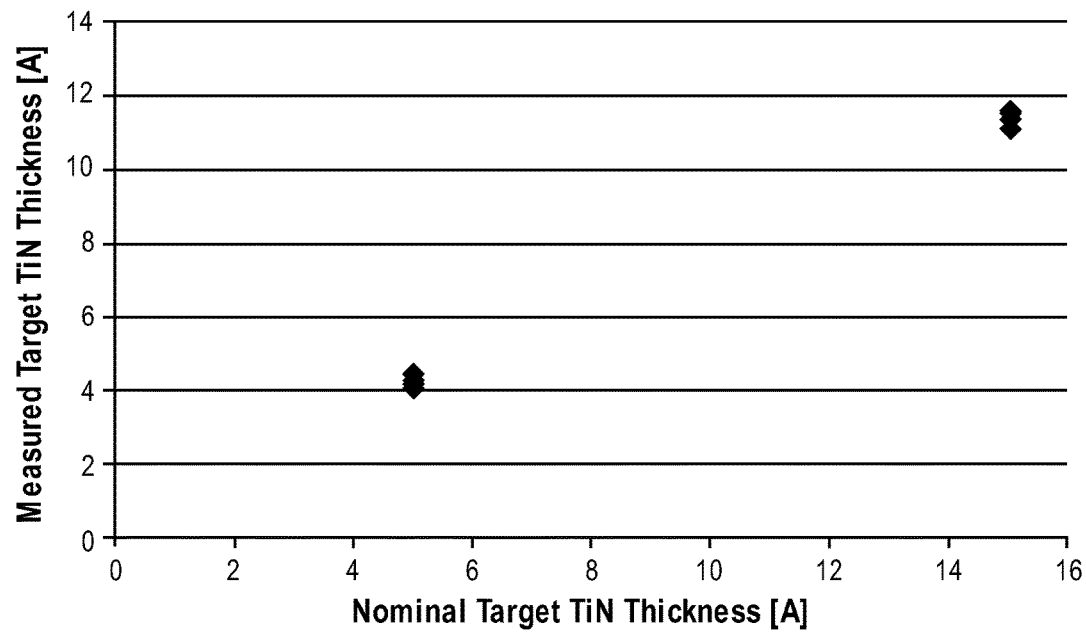
FIG. 2 is a plot corresponding to a first operation in a feed-forward process, in accordance with an embodiment of the present invention.

FIG. 2 is a plot 200 corresponding to a first operation in a feed-forward process, in accordance with an embodiment of the present invention. Referring to plot 200, measured titanium nitride (TiN) thickness in Angstroms (A) is plotted as a function of nominal target TiN thickness. It is to be appreciated that the measurement may be TiN only or may be TiN and HiK as a combination. In an embodiment, for the first measurement operation (plot 200), results for each wafer TiN thickness split are saved in a feed-forward database.

Figure 3:
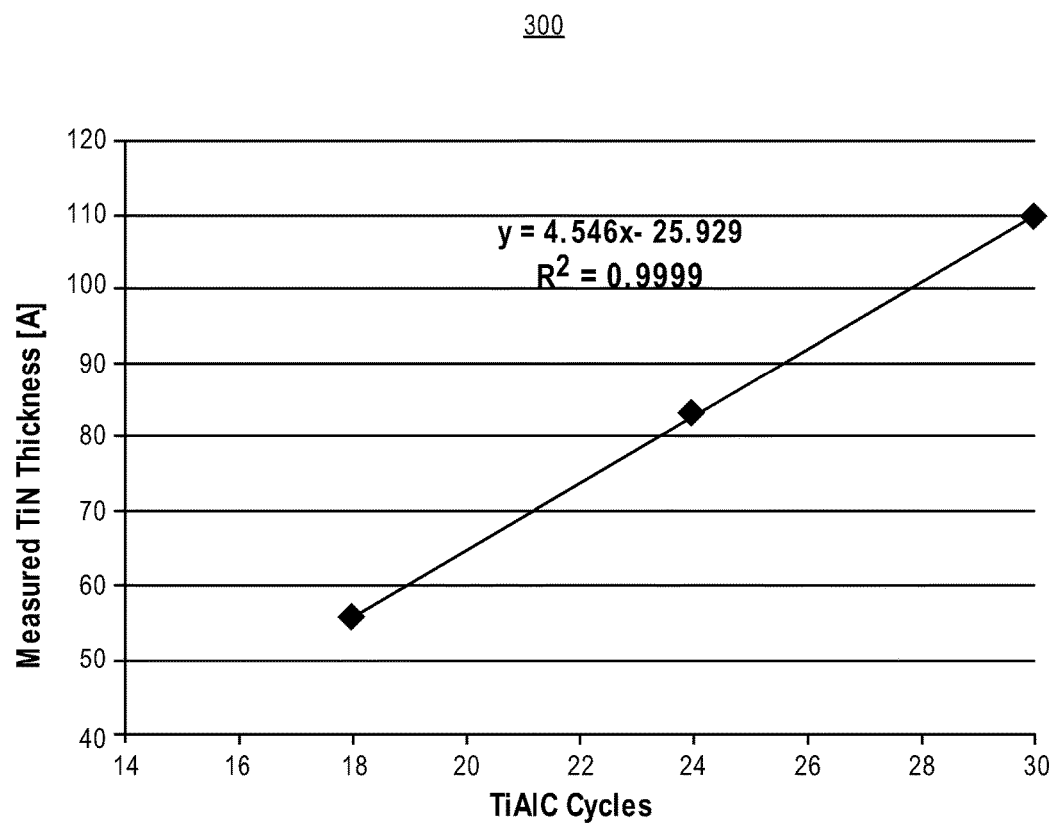
FIG. 3 is a plot corresponding to a second operation in the feed-forward process, in accordance with an embodiment of the present invention.

FIG. 3 is a plot 300 corresponding to a second operation in the feed-forward process, in accordance with an embodiment of the present invention. Referring to plot 300, measured titanium aluminum carbide (TiAlC) thickness in Angstroms (A) is plotted as a function of TiAlC deposition cycles, where the TiAlC is deposited above the TiN/HiK of the first operation. The TiN/Hik thickness results from the first operation are fed-forward site-by-site to the second process and measurement operation (to generate plot 300). Thus, the second operation involves deposition and measurement of TiAlC, the measurement involving use of thickness results from the first operation.

Figure 4:
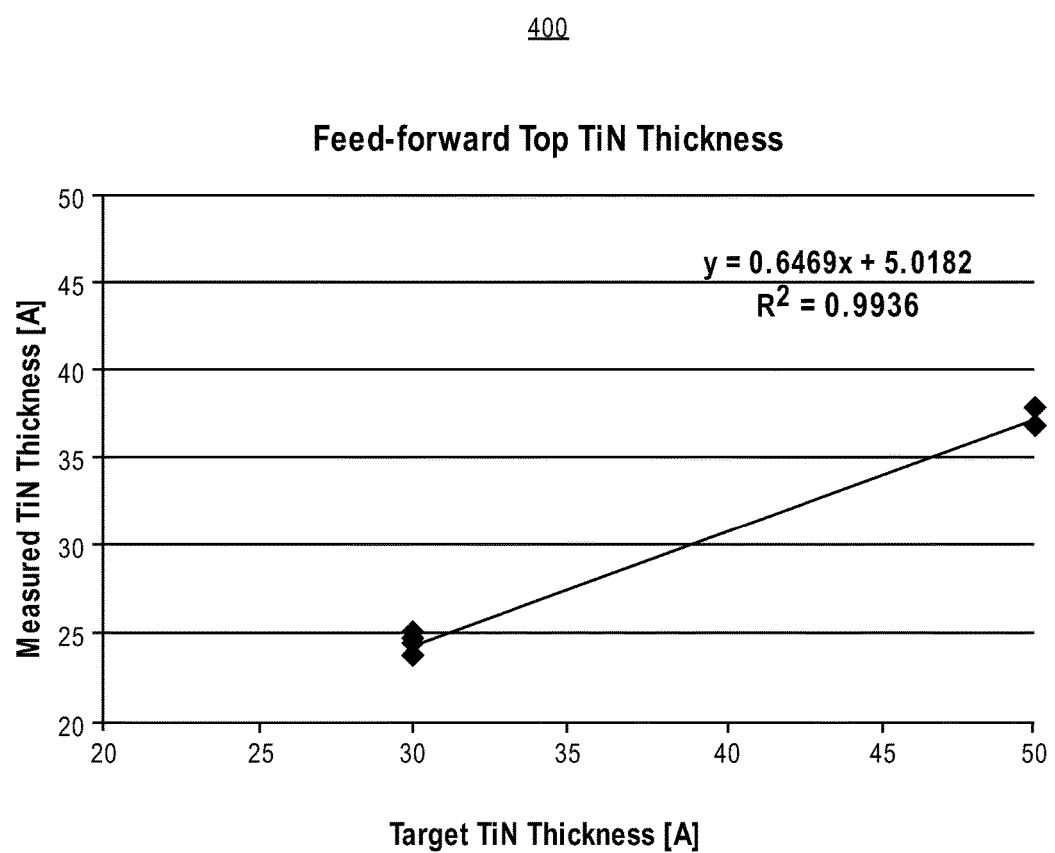
FIG. 4 is a plot corresponding to a third operation in the feed-forward process, in accordance with an embodiment of the present invention.

FIG. 4 is a plot 400 corresponding to a third operation in the feed-forward process, in accordance with an embodiment of the present invention. Referring to plot 400, measured titanium nitride (TiN) thickness in Angstroms (A) is plotted as a function of target TiN thickness. The TiN is deposited above TiAlC of the second operation. The top TiN film thickness at this third operation is determined using results from previous two process operations. Thus, the third deposition and measurement operation is top TiN, using the thickness results from the first and second operations described above. The linearity of the measured results with the expected result at each operation is clearly demonstrated in plot 400.

As a second specific example of a multi-operation/multi-process film result using a feed forward approach, a three-operation $ZrO_2/Al_2O_3/ZrO_2$/Substrate (ZAZ/Substrate) application is described below in association with FIGS. 5 and 6.

Figure 5:
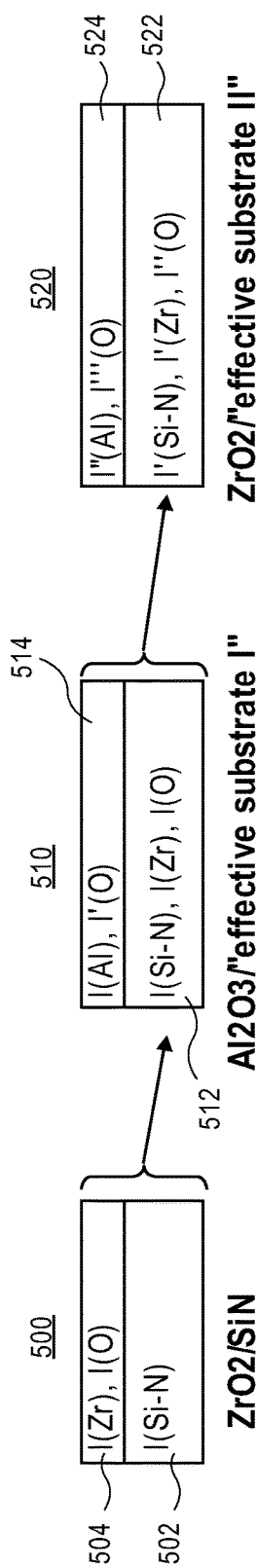
FIG. 5 illustrates a three-operation ZAZ application involving $ZrO_2 \rightarrow Al_2O_3/ZrO_2 \rightarrow ZrO_2/Al_2O_3/ZrO_2$, in accordance with an embodiment of the present invention.

FIG. 5 illustrates a three-operation ZAZ application involving $ZrO_2 \rightarrow Al_2O_3/ZrO_2 \rightarrow ZrO_2/Al_2O_3/ZrO_2$, in accordance with an embodiment of the present invention. Referring to FIG. 5, structure 500 includes a layer of zirconium oxide ($ZrO_2$) 504 on silicon nitride (SiN) layer 502. The $ZrO_2$ layer 504 is associated with a signal intensity for zirconium (I(Zr)) and an intensity signal for oxygen (I(O)). The SiN layer 502 is associated with a signal intensity for silicon nitride (I(Si—N)). When determining a thickness of the $ZrO_2$ layer 504, the underlying I(Si—N) intensity signal is attributed to the underlying SiN "substrate."

For the next structure 510 of FIG. 5, an aluminum oxide ($Al_2O_3$) layer 514 has been deposited on the structure 500. The $Al_2O_3$ layer 514 is associated with a signal intensity for aluminum (I(Al)) and an intensity signal for oxygen (I'(O)). When determining a thickness of the $Al_2O_3$ layer 514, the underlying I(Si—N), I(Zr) and I(O) intensity signals are attributed to an underlying "effective substrate I" 512 that accounts for intensity signals from the SiN 502 and the $ZrO_2$ layers 504 from the structure 500.

For the next structure 520 of FIG. 5, a second zirconium oxide ($ZrO_2$) layer 524 has been deposited on the structure 510. The $ZrO_2$ layer 524 is associated with a signal intensity for zirconium (I"(Zr)) and an intensity signal for oxygen (I'''(O)). When determining a thickness of the $ZrO_2$ layer 524, the underlying I'(Si—N), I'(Zr), I"(O) and I(Al) intensity signals are attributed to an underlying "effective substrate II" 522 that accounts for intensity signals from the SiN layer 502, the first $ZrO_2$ layer 504 and the $Al_2O_3$ layer 514.

Figure 6:
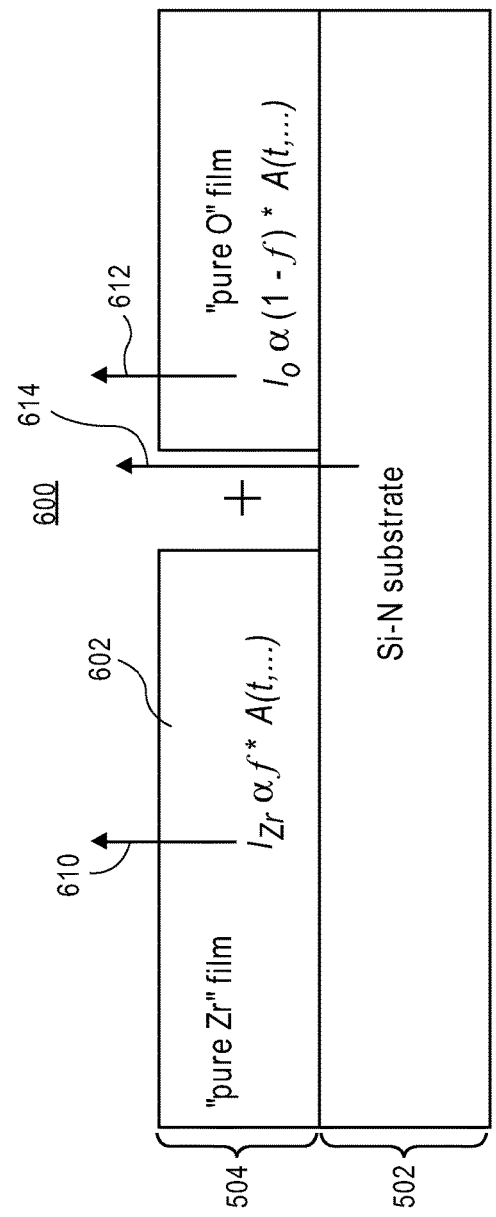
FIG. 6 illsutrates a mixing model used to characterize the $ZrO_2$ film of FIG. 5, in accordance with an embodiment of the present invention.

FIG. 6 illsutrates a mixing model used to characterize the $ZrO_2$ layer 504 of FIG. 5, in accordance with an embodiment of the present invention. Referring to FIG. 6, the $ZrO_2$ layer 504 is modeled as a mixing model 600, where the connection between the film AC % and mixing fraction is defined. In particular, the $ZrO_2$ layer 504 is modeled as a "pure Zr" film component 602 and a "pure O" film component 604. This provides relative intensity signals for Zr (signal 610), O (signal 612) and the underlying SiN substrate 502 (signal 614). Referring again to FIG. 5, at the operation concerning structure 510, the intensity response of all prior species from the model 600 is encoded as an effective substrate 512 with relative intensities calculated from the first operation (i.e., the operation illustrated in FIG. 6).

In another aspect of embodiments of the present invention, a film measurement system includes both an XPS detector and an XRF detector. For example, FIG. 7 is an illustration representing a film measurement system having XPS and XRF detection capability, in accordance with an embodiment of the present invention.

Figure 7:
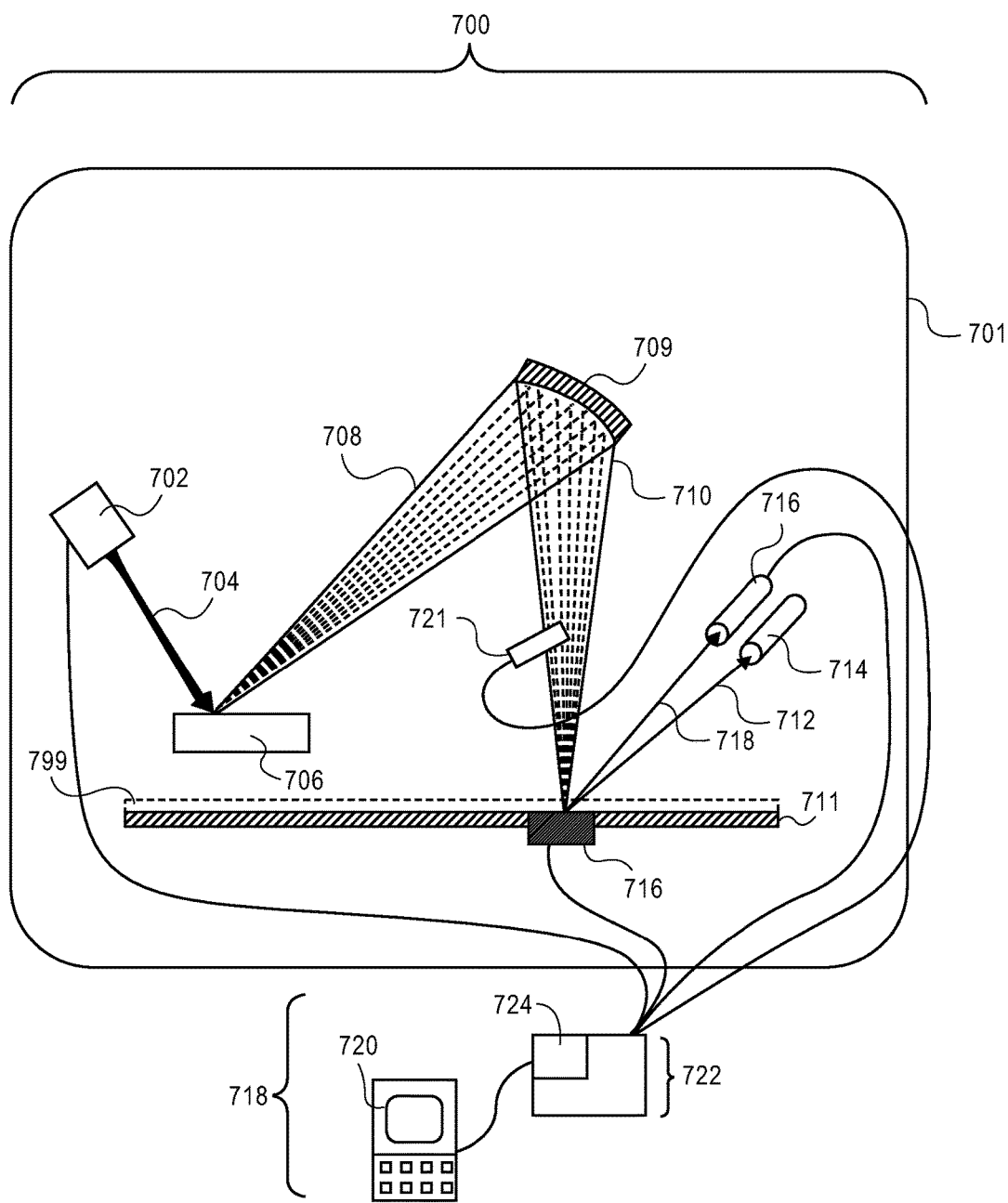
FIG. 7 is an illustration representing a film measurement system having XPS and XRF detection capability, in accordance with an embodiment of the present invention.

Referring to FIG. 7, a film measurement system 700 includes an XPS/XRF generation and detection system housed in a chamber 701 coupled with a computing system 722. The XPS/XRF generation and detection system includes an electron beam source 702 provided for generating an electron beam 704. Electron beam 704 is used to generate an X-ray beam 708 by bombarding an anode 706. A monochromator 709 is provided for transporting a monochromatized X-ray beam 710 from X-ray beam 708. A sample holder 711 may be used to position a sample 799 in a pathway of monochromatized X-ray beam 710.

An XPS detector 714 is provided for collecting an XPS signal 712 generated by bombarding sample 799 with monochromatized X-ray beam 710. An XRF detector 716 is provided for collecting an XRF signal 718 also generated by bombarding sample 799 with monochromatized X-ray beam 710. In an embodiment, system 700 is configured to collect XRF signal 718 and XPS signal 712 simultaneously or near simultaneously, representing a single sampling event. The XPS signal 712 and XRF signal 718 are composed of photo-electrons and fluorescent X-rays, respectively. Additionally, a flux detector 720 may be provided for determining an estimated flux of monochromatized X-ray beam 710. In one such embodiment, flux detector 720 is positioned at sample holder 711, as depicted in FIG. 7. In another embodiment, an X-ray flux detector 721 is placed near the monochromator to partially intersect a small fraction of the primary X-rays in order to monitor the X-ray flux while the sample holder 711 is positioned at the analysis site, as is depicted in FIG. 7.

Computing system 722 includes a user interface 724 coupled with a computing portion 726 having a memory portion 728. Computing system 722 may be configured to calibrate an XPS signal detected by XPS detector 714. Computing system 722 may be configured to calibrate the XRF signal detected by XRF detector 716. Computing system 722 may be configured to monitor the primary X-ray flux as measured by Flux detector 720 and/or 721. In accordance with an embodiment of the present invention, computing system 722 is for normalizing an XPS signal detected by XPS detector 714, as well as an XRF signal detected by XRF detector 716 with the primary X-ray flux measured by Flux detector 720 or 721. In one embodiment, memory portion 728 has stored thereon a set of instructions for, when executed, using monochromatized X-ray beam 710 to generate XPS signal 712 and XRF signal 718 from sample 799.

Figure 8:
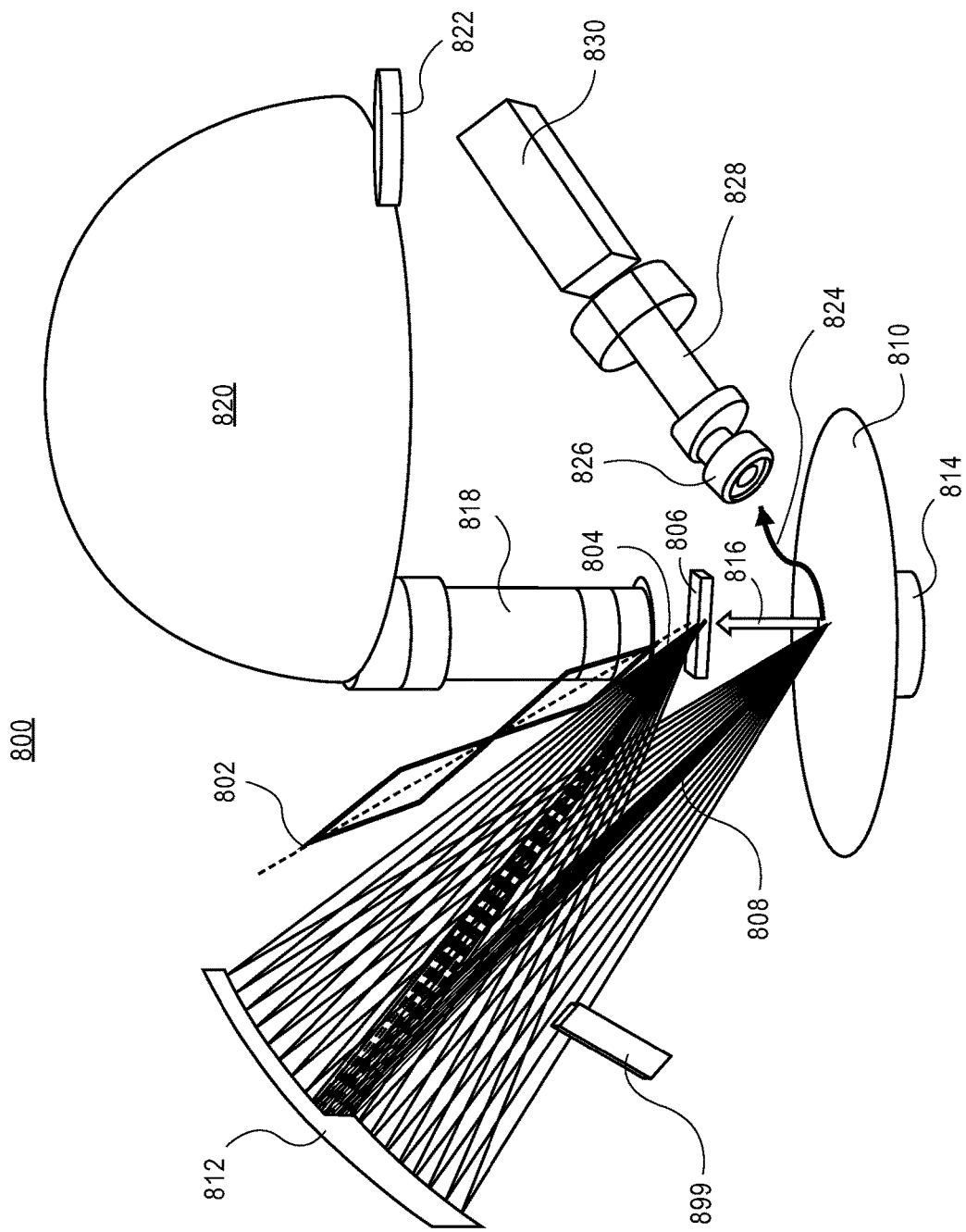
FIG. 8 is an illustration representing another film measurement system having XPS and XRF detection capability, in accordance with an embodiment of the present invention.

FIG. 8 is an illustration representing another film measurement system having XPS and XRF detection capability, wherein both XPS and XRF information may be obtained from a single metrology tool, in accordance with an embodiment of the present invention. In FIG. 8, an angled view of an XPS and XRF combination tool 800 is depicted. In one embodiment, the XPS and XRF combination tool 100 is capable of measuring 300 mm wafers within a 50 $\mu m^2$ metrology box.

Referring to FIG. 8, the XPS and XRF combination tool 800 is operated while maintained under a base pressure of less than approximately 1.0E-7 Torr. Using a $LaB_6$ electron gun 802 at a nominal beam current of approximately 600 $\mu A$, x-rays 804 are generated from an aluminum anode 806 at 1486.7 eV. Monochromatic AlKα x-rays 808 is then focused on to a wafer 810 by a high quality quartz crystal monochromator 812. A magnetic lens 814 under the wafer 810 generates a magnetic field near the wafer 810 surface and focuses the photoelectrons 816 generated into an XPS spectrometer including XPS input optics 818, an XPS energy analyzer 820 (e.g., a Spherical Capacitor Analyzer (SCA)), and an XPS detector 822. The XPS spectrometer electron optics 818 directs and shapes the photoelectron beam 816 for best transmission into the XPS energy analyzer 820. The XPS energy analyzer 820 operates at fixed voltage difference between the spheres, and a pass energy of 141.2 eV is typically used.

Referring again to FIG. 1, simultaneously, the monochromatic AlKα x-rays 808 excites low energy x-ray fluorescence (LE-XRF) 824 from the wafer 810. The LE-XRF 824 is detected by using a Silicon Drift Detector (SDD) 826 located near the analysis point, approximately 1 mm above the wafer 810 surface. In one embodiment, the SDD detector 826 is cooled by dual Peltier coolers, and the operating temperature is maintained at approximately −30° C. To filter out stray electrons and UV light, an ultrathin aluminum window may be used at the SDD 826 entrance. SDD 826 is coupled to an XRF detector assembly 828. The XRF detector assembly 828 is coupled to SDD electronics 830.

The XPS and XRF combination tool 800 may also include a post-monochromator flux detector 899, as is depicted in FIG. 8. Although not depicted, XPS and XRF combination tool 800 may also be equipped with vision cameras. For example, a wafer-XY camera can be included for feature finding and pattern recognition on the wafer. A wafer-Z camera can be included for determining the wafer z-height for optimal x-ray spot focusing and positioning. An anode camera can be included that monitors the anode for optimal e-beam focus and position. Data acquisition may be integrated to the system software where both XPS and XRF signals are collected at the same time. In one such embodiment, total acquisition time is approximately 24 s per site.

Figure 9:
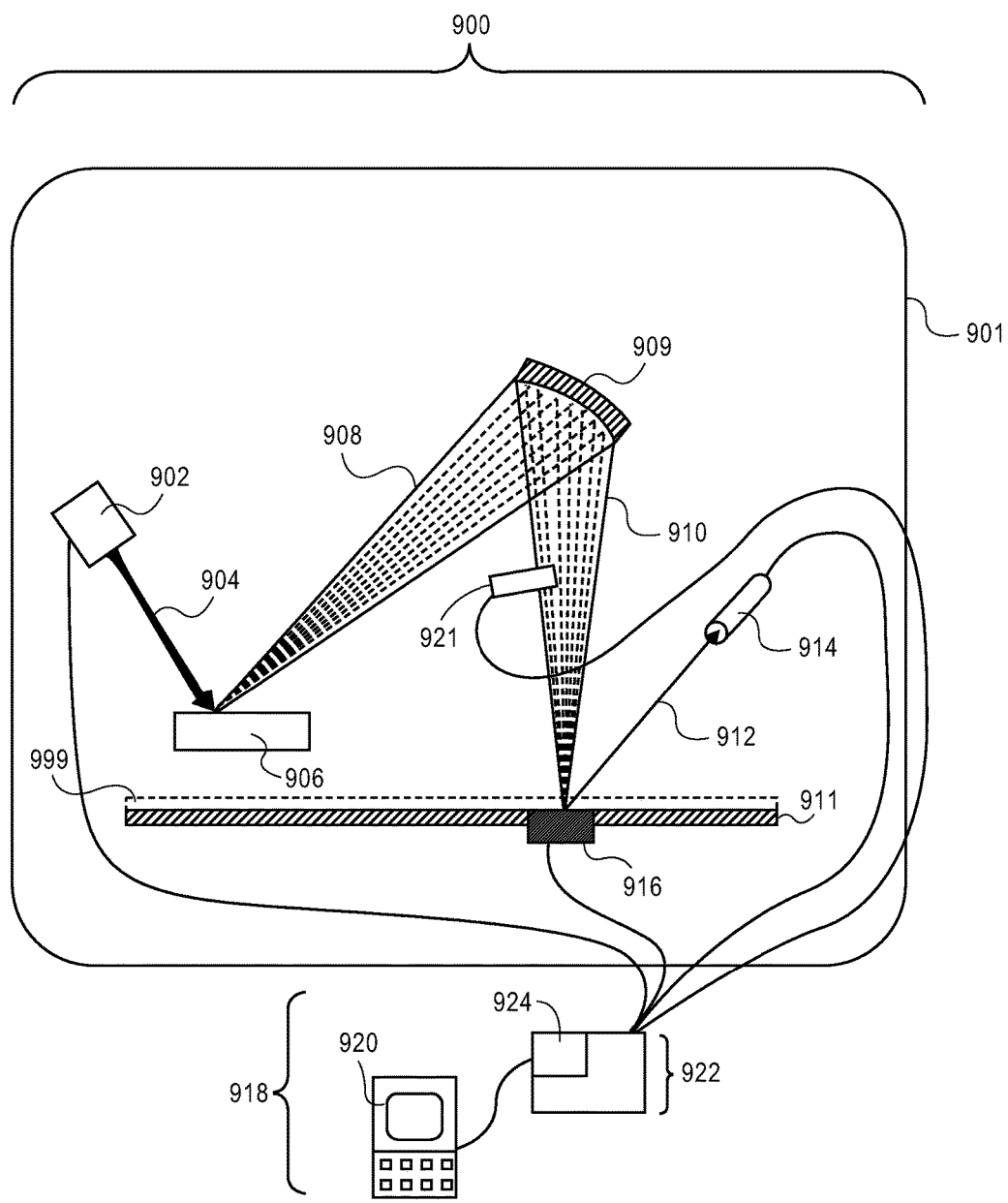
FIG. 9 is an illustration representing a film measurement system having XPS detection capability, in accordance with an embodiment of the present invention.

Although several of the above described embodiments involve feed-forward techniques for a combination of XPS and XRF measurements, it is to be appreciated that such techniques are also applicable for XRF measurements on their own, or for XPS measurements on their own. Accordingly, a suitable measurement apparatus may not be equipped with both XRF and XPS measurement capabilities, but may be equipped with only one of XRF or XPS measurement capabilities. As an example, FIG. 9 is an illustration representing a film measurement system having only XPS detection capability, in accordance with an embodiment of the present invention. As another example, although not depicted, a film measurement system has only XRF detection capability.

Referring to FIG. 9, a film measurement system 900 includes an XPS generation and detection system housed in a chamber 901 coupled with a computing system 918. Computing system 918 includes a user interface 920 coupled with a computing portion 922 having a memory portion 924. The XPS generation and detection system includes an electron beam source 902 provided for generating an electron beam 904. Electron beam 904 is used to generate an X-ray beam 908 by bombarding an anode 906. A monochromator 909 is provided for focusing a monochromatized X-ray beam 910 from X-ray beam 908. A sample holder 911 may be used to position a sample 999 in a pathway of monochromatized X-ray beam 910.

An XPS detector 914 is provided for collecting an XPS signal 912 generated by bombarding sample 999 with monochromatized X-ray beam 910. Additionally, a flux detector 916 may be provided for determining an estimated flux of monochromatized X-ray beam 910. In one such embodiment, flux detector 916 is positioned at sample holder 911, as depicted in FIG. 9. In another embodiment, an X-ray flux detector 921 is placed near the monochromator to partially intersect a small fraction of the primary X-rays in order to monitor the X-ray flux while the sample holder 911 is positioned at the analysis site.

In an embodiment, whether a system is equipped with XPS detection capability only or both XPS and XRF detection capability, a method of thin film characterization includes measuring a first XPS intensity signal for a sample having a first layer above a substrate. The first XPS intensity signal includes information for the first layer and for the substrate. The method also involves determining a thickness of the first layer based on the first XPS intensity signal. The method also involves combining the information for the first layer and for the substrate to estimate an effective substrate. The method also involves measuring a second XPS intensity signal for a sample having a second layer above the first layer above the substrate. The second XPS intensity signal includes information for the second layer, for the first layer and for the substrate. The method also involves determining a thickness of the second layer based on the second XPS intensity signal, the thickness accounting for the effective substrate.

In another embodiment, whether a system is equipped with XRF detection capability only or both XPS and XRF detection capability, a method of thin film characterization includes measuring a first XRF intensity signal for a sample having a first layer above a substrate. The first XRF intensity signal includes information for the first layer and for the substrate. The method also involves determining a thickness of the first layer based on the first XRF intensity signal. The method also involves combining the information for the first layer and for the substrate to estimate an effective substrate. The method also involves measuring a second XRF intensity signal for a sample having a second layer above the first layer above the substrate. The second XRF intensity signal includes information for the second layer, for the first layer and for the substrate. The method also involves determining a thickness of the second layer based on the second XRF intensity signal, the thickness accounting for the effective substrate.

Embodiments of the present invention may be provided as a computer program product, or software, that may include a machine-readable medium having stored thereon instructions, which may be used to program a computer system (or other electronic devices) to perform a process according to the present invention. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., infrared signals, digital signals, etc.)), etc.

Figure 10:
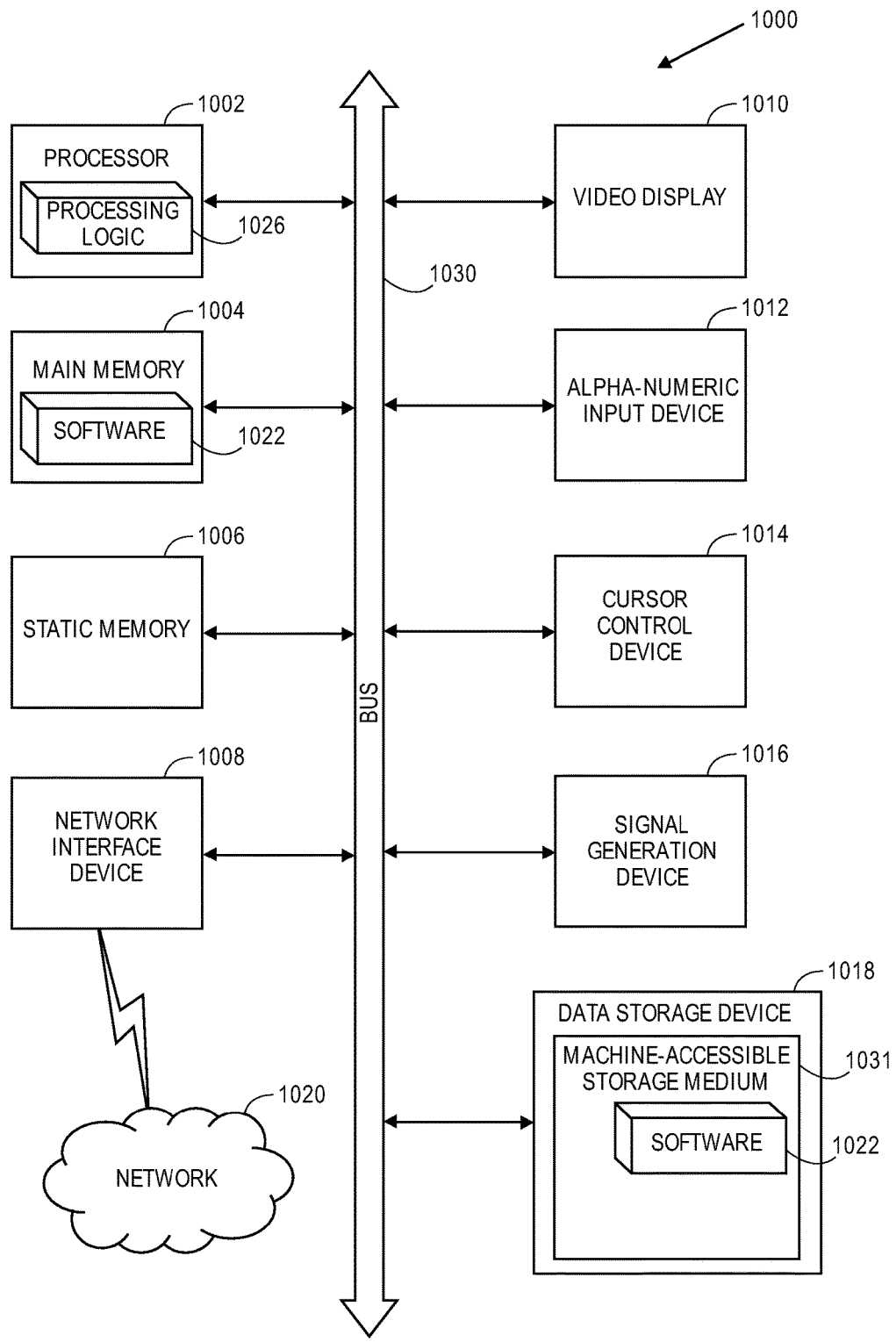
FIG. 10 illustrates a block diagram of an exemplary computer system, in accordance with an embodiment of the present invention.

FIG. 10 illustrates a diagrammatic representation of a machine in the exemplary form of a computer system 1000 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 1000 includes a processor 1002, a main memory 1004 (e.g., read-only memory (ROM), flash memory, dynamic random access memory (DRAM) such as synchronous DRAM (SDRAM) or Rambus DRAM (RDRAM), etc.), a static memory 1006 (e.g., flash memory, static random access memory (SRAM), etc.), and a secondary memory 1018 (e.g., a data storage device), which communicate with each other via a bus 1030.

Processor 1002 represents one or more general-purpose processing devices such as a microprocessor, central processing unit, or the like. More particularly, the processor 1002 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 1002 may also be one or more special-purpose processing devices such as an application specific integrated circuit (ASIC), a field programmable gate array (FPGA), a digital signal processor (DSP), network processor, or the like. Processor 1002 is configured to execute the processing logic 1026 for performing the operations discussed herein.

The computer system 1000 may further include a network interface device 1008. The computer system 1000 also may include a video display unit 1010 (e.g., a liquid crystal display (LCD) or a cathode ray tube (CRT)), an alphanumeric input device 1012 (e.g., a keyboard), a cursor control device 1014 (e.g., a mouse), and a signal generation device 1016 (e.g., a speaker).

The secondary memory 1018 may include a machine-accessible storage medium (or more specifically a computer-readable storage medium) 1031 on which is stored one or more sets of instructions (e.g., software 1022) embodying any one or more of the methodologies or functions described herein. The software 1022 may also reside, completely or at least partially, within the main memory 1004 and/or within the processor 1002 during execution thereof by the computer system 1000, the main memory 1004 and the processor 1002 also constituting machine-readable storage media. The software 1022 may further be transmitted or received over a network 1020 via the network interface device 1008.

While the machine-accessible storage medium 1031 is shown in an exemplary embodiment to be a single medium, the term "machine-readable storage medium" should be taken to include a single medium or multiple media (e.g., a centralized or distributed database, and/or associated caches and servers) that store the one or more sets of instructions.

The term "machine-readable storage medium" shall also be taken to include any medium that is capable of storing or encoding a set of instructions for execution by the machine and that cause the machine to perform any one or more of the methodologies of the present invention. The term "machine-readable storage medium" shall accordingly be taken to include, but not be limited to, solid-state memories, and optical and magnetic media.

In an embodiment, a non-transitory machine-accessible storage medium having instructions stored thereon which cause a data processing system to perform a method of method of thin film characterization. The method includes measuring first XPS and XRF intensity signals for a sample having a first layer above a substrate. The first XPS and XRF intensity signals include information for the first layer and for the substrate. The method also involves determining a thickness of the first layer based on the first XPS and XRF intensity signals. The method also involves combining the information for the first layer and for the substrate to estimate an effective substrate. The method also involves measuring second XPS and XRF intensity signals for a sample having a second layer above the first layer above the substrate. The second XPS and XRF intensity signals include information for the second layer, for the first layer and for the substrate. The method also involves determining a thickness of the second layer based on the second XPS and XRF intensity signals, the thickness accounting for the effective substrate.

Thus, methods and systems for feed-forward of multi-layer and multi-process information using XPS and XRF technologies have been described.

What is claimed is:

1. A method of thin film characterization, the method comprising:
   measuring first XPS and/or XRF intensity signals for a sample having a first layer above a substrate, the first XPS and/or XRF intensity signals including information for the first layer and for the substrate;
   determining a thickness of the first layer based on the first XPS and/or XRF intensity signals;
   combining the information for the first layer and for the substrate to estimate an effective substrate;
   measuring second XPS and/or XRF intensity signals for a sample having a second layer above the first layer above the substrate, the second XPS and/or XRF intensity signals including information for the second layer, for the first layer and for the substrate; and
   determining a thickness of the second layer based on the second XPS and/or XRF intensity signals, the thickness accounting for the effective substrate.

2. The method of claim 1, wherein combining the information for the first layer and for the substrate to estimate the effective substrate comprises combining signals in a global, simultaneous fit by direct or model-based methods.

3. The method of claim 1, wherein estimating the effective substrate comprises using an effective substrate model based on atomic species from the first layer and the substrate, and an intensity production factor that scales with a bulk atomic composition % value for the atomic species.

4. The method of claim 3, wherein the second layer comprises an atomic species not included in the substrate or the first layer.

5. The method of claim 1, wherein estimating the effective substrate is a model-independent approach based on fundamental atomic sensitivity factors (ASFs).

6. The method of claim 1, wherein determining the thickness of the second layer based on the second XPS and/or XRF intensity signals further comprises determining a composition for the second layer based on the second XPS and/or XRF intensity signals, the composition accounting for the effective substrate.

7. The method of claim 1, further comprising:
   combining the information for the second layer, the first layer and for the substrate to estimate a second effective substrate;
   measuring third XPS and/or XRF intensity signals for a sample having a third layer above the second layer above the first layer above the substrate, the third XPS and/or XRF intensity signals including information for the third layer, for the second layer, for the first layer and for the substrate; and
   determining a thickness of the third layer based on the third XPS and/or XRF intensity signals, the thickness accounting for the second effective substrate.

8. A system for characterizing a thin film, said system comprising:
   an X-ray source for generating an X-ray beam;
   a sample holder for positioning a sample in a pathway of said X-ray beam;
   a first detector for collecting an X-ray photoelectron spectroscopy (XPS) signal generated by bombarding said sample with said X-ray beam;
   a second detector for collecting an X-ray fluorescence (XRF) signal generated by bombarding said sample with said X-ray beam; and
   a computing device configured to determine a thickness of a second layer of the sample based on the XPS and XRF signals, wherein determining the thickness accounts for an estimated effective substrate based on a first layer and a substrate of the sample, the first layer and substrate below the second layer of the sample.

9. The system of claim 8, wherein the first detector and the second detector are configured to collect the XPS signal and the XRF signal, respectively, at the same time.

10. The system of claim 8, wherein the first detector and the second detector are configured to collect the XPS signal and the XRF signal from within an approximately 50 $\mu m^2$ metrology box of the sample.

11. The system of claim 8, further comprising:
    a post-monochromator flux detector for normalizing the XRF signal with respect to an incoming x-ray flux for stable measurement.

12. The system of claim 8, wherein the system is maintained under a base pressure of less than approximately 1.0E-7 Torr during the collecting the XPS signal and the XRF signal.

13. The system of claim 8, wherein the X-ray beam is monochromatic AlK$\alpha$ x-ray beam.

14. The system of claim 8, further comprising:
    a quartz monochromator disposed along the pathway of the X-ray beam, between the X-ray source and the sample holder.

15. A non-transitory machine-accessible storage medium having instructions stored thereon which cause a data processing system to perform a method of method of thin film characterization, the method comprising:
    measuring first XPS and/or XRF intensity signals for a sample having a first layer above a substrate, the first XPS and/or XRF intensity signals including information for the first layer and for the substrate;
    determining a thickness of the first layer based on the first XPS and/or XRF intensity signals;
    combining the information for the first layer and for the substrate to estimate an effective substrate;

measuring second XPS and/or XRF intensity signals for a sample having a second layer above the first layer above the substrate, the second XPS and/or XRF intensity signals including information for the second layer, for the first layer and for the substrate; and determining a thickness of the second layer based on the second XPS and/or XRF intensity signals, the thickness accounting for the effective substrate.

16. The storage medium as in claim 15, wherein combining the information for the first layer and for the substrate to estimate the effective substrate comprises combining signals in a global, simultaneous fit by direct or model-based methods.

17. The storage medium as in claim 15, wherein estimating the effective substrate comprises using an effective substrate model based on atomic species from the first layer and the substrate, and an intensity production factor that scales with a bulk atomic composition % value for the atomic species.

18. The storage medium as in claim 17, wherein the second layer comprises an atomic species not included in the substrate or the first layer.

19. The storage medium as in claim 15, wherein estimating the effective substrate is a model-independent approach based on fundamental atomic sensitivity factors (ASFs).

20. The storage medium as in claim 15, wherein determining the thickness of the second layer based on the second XPS and/or XRF intensity signals further comprises determining a composition for the second layer based on the second XPS and/or XRF intensity signals, the composition accounting for the effective substrate.

* * * * *